US00PP09212P

United States Patent [19]

Trees

[11] Patent Number: Plant 9,212

[45] Date of Patent: Jul. 25, 1995

[54] NEW GUINEA IMPATIENS NAMED RASPBERRY ROSE

[75] Inventor: Scott C. Trees, Arroyo Grande, Calif.

[73] Assignee: Geo. J. Ball, Inc., West Chicago, Ill.

[21] Appl. No.: 338,155

[22] Filed: Nov. 8, 1994

[51] Int. Cl.[6] ..... A01H 5/00

[52] U.S. Cl. ..... Plt./87.6

[58] Field of Search ..... Plt. 87.6

[56] References Cited

U.S. PATENT DOCUMENTS

P.P. 8,264 6/1993 Dehan ..... Plt./87.6

*Primary Examiner*—James R. Feyrer

*Attorney, Agent, or Firm*—Burns, Doane, Swecker & Mathis

[57] ABSTRACT

A new and distinct New Guinea Impatiens cultivar named Raspberry Rose is provided. This new cultivar was the result of a controlled breeding program wherein a plant designated N2507-3 (non-patented in the United States) was pollinated by a plant designated 3616-A (non-patented in the United States). The new cultivar forms large dark rose colored flowers with a white eye which exhibit an iridescent appearance, forms medium green foliage, and displays a moderate growth habit. The new cultivar can be readily distinguished from the Danserra cultivar (U.S. Plant Pat. No. 8,264).

1 Drawing Sheet

SUMMARY OF THE INVENTION

The present invention comprises a new and distinctive Impatiens plant, botanically known as New Guinea Impatiens, and hereinafter is referred to by the cultivar name Raspberry Rose.

The new cultivar is the product of a planned breeding program. More specifically, the breeding program which resulted in the production of the new cultivar was carried out in a controlled environment during 1991 at Arroyo Grande, Calif., U.S.A. The female parent (i.e., the seed parent) was a plant designated N2507-3 (non-patented in the United States) which exhibits bright salmon pink flowers with medium green foliage. The male parent (i.e., the pollen parent) was a plant designated 3616-A (non-patented in the United States) which exhibits very large rose colored flowers, dark green foliage, and a vigorous growth habit. The parentage of the new cultivar can be summarized as follows:

N2507-3×3616-A.

The seeds resulting from the above pollination were sown and plantlets were obtained which were physically and biologically different from each other. Selective study resulted in the identification of a single plant of the new cultivar. This plant had large rose colored flowers and initially was designated BFP-400.

It was found that the new cultivar of the present invention:

(a) exhibits attractive large dark rose colored flowers with a white eye,
(b) forms medium green foliage,
(c) exhibits a good basal branching character, and
(d) exhibits a medium upright growth habit.

Asexual reproduction of the new cultivar by terminal or stem cuttings during 1993, at Arroyo Grande, Calif., U.S.A. has demonstrated that the characteristics of the new cultivar as herein described are firmly fixed and are retained through successive generations of such asexual propagation.

The Raspberry Rose cultivar has not been observed under all possible environmental conditions to date. Accordingly, it is possible that the phenotype may vary somewhat with variations in the environment, such as temperature, light intensity, and day length.

When the new cultivar of the present invention is compared to the Danserra cultivar (U.S. Plant Pat. No. 8,264), it is found that the new cultivar exhibits flowers having larger petals that include a distinctive white eye.

When plant material of the Raspberry Rose cultivar is subjected to standard random amplified polymorphic DNA marker analysis (RAPD) using polymerase chain reaction (PCR) and a known unique set of DNA primers, it is found to exhibit a different fingerprint map when compared to that of the Danserra cultivar which confirms its genetic distinctiveness.

Plants of the new cultivar will be marketed under the Celebration trademark by Geo. J. Ball, Inc.

BRIEF DESCRIPTION OF THE PHOTOGRAPH

The accompanying photograph shows as nearly true as it is reasonably possible to make the same in a color illustration of this character, a typical specimen of an overall plant of the new cultivar. The plant was grown in a greenhouse at West Chicago, Ill., U.S.A.

DETAILED DESCRIPTION

The chart used in the identification of colors described herein is the R.H.S. Colour Chart of the Royal Horticultural Society, London, England. The color values were determined during the third week of July, 1994. The readings were taken between 10:00 and 11:00 a.m. under 2,000 footcandles of light at West Chicago, Ill., U.S.A. The plants were produced from cuttings taken from stock plants and were grown under greenhouse conditions comparable to those used in commerical practice while utilizing a soilless growth medium and maintaining temperatures of approximately 72° F. during the day and approximately 65° F. during the night.

Propagation:

*Type cutting.*—Terminal tip.

*Time to initiate roots.*—Approximately 14 to 21 days with the shorter times generally being experienced in the summer and the longer times in the winter.

*Rooting habit.*—Fibrous, and branching.

Plant description:

*Form.*—Basal branching.

*Habit of growth.*—Medium upright mounded. A mature plant commonly measures approximately 15 to 18 cm. in height and approximately 28 to 30 cm. in width.

*Foliage.*—The configuration is narrow and lanceolate. The leaves commonly measure approximately 9.8 cm. in length and approximately 3.6 cm. in width. This can be compared to a length of approximately 9.3 cm. and a width of approximately 2.7 cm. for the Danserra cultivar. The foliage of the new cultivar is Green Group 139A (adaxial) and Green Group 137C (abaxial). This can be compared to Green Group 137A (adaxial) and Green Group 137D (abaxial) for the Danserra cultivar. The stem color is Yellow-Green Group 145A for the new cultivar. This can be compared to Yellow-Green Group 145B for the Danserra cultivar.

Flower description:

Flowering habit.—Freely flowering.

*Natural flowering season.*—Throughout the year in a greenhouse environment.

*Flowers borne.*—Above the foliage arising from leaf axils.

*Flower color.*—Red-Purple Group 66A with white adjacent the attachment points thereby forming an eye (adaxial), and Red-Purple Group 66C (abaxial). This can be compared to Red-Purple Group 57A (adaxial) and Red-Purple Group 57B (abaxial) for the Danserra cultivar.

*Quantity of flowers.*—Approximately 8 to 12 per stem for both the Raspberry Rose and Danserra cultivars.

*Number of petals.*—Five.

*Flower size.*—Approximately 5.5 to 5.8 cm. in length and approximately 5.2 to 5.5 cm. in width. This can be compared to a length of approximately 5.0 to 5.1 cm. and a width of approximately 4.3 to 4.6 cm. for the Danserra cultivar.

*Nectary length.*—Approximately 5.7 cm. which can be compared to approximately 4.1 cm. for the Danserra cultivar.

*Nectary color.*—Red Group 42B which can be compared to Red Group 53A for the Danserra cultivar.

*Reproductive organs.*—The anthers are fused together forming one organ that surrounds the pistil. Generally, the anthers shed pollen prior to the stigma becoming receptive. The pollen color is Yellow Group 10D, the stigma color is Yellow-Green Group 154D, and the ovary color is Yellow-Green Group 144C for both the Raspberry Rose and the Danserra cultivars.

I claim:

1. A new and distinct cultivar of New Guinea Impatiens named Raspberry Rose susbtantially as herein shown and described, which:

(a) exhibits attractive large dark rose colored flowers with a white eye, (b) forms medium green foliage, (c) exhibits a good basal branching character, and (d) exhibits a medium upright growth habit.

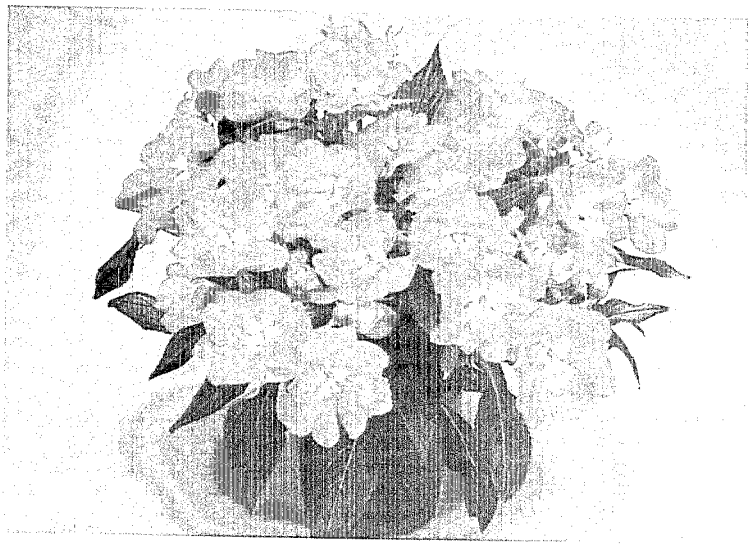

* * * * *